United States Patent [19]
Reilly

[11] Patent Number: 5,470,588
[45] Date of Patent: * Nov. 28, 1995

[54] METHOD OF INCREASING VAGINAL LUBRICATION

[76] Inventor: Susann R. Reilly, 300 Commercial St., Apt. #412, Boston, Mass. 02109

[*] Notice: The portion of the term of this patent subsequent to Jan. 25, 2011, has been disclaimed.

[21] Appl. No.: 170,151

[22] Filed: Dec. 20, 1993

Related U.S. Application Data

[63] Continuation-in-part of Ser. No. 862,454, Apr. 2, 1992, Pat. No. 5,231,423.

[51] Int. Cl.$^6$ ............................................. A61K 33/36
[52] U.S. Cl. ............................................. 424/667; 424/662
[58] Field of Search ..................................... 424/662, 667

[56] References Cited

U.S. PATENT DOCUMENTS 4,670,256  6/1987  Doran ........................................ 424/93

OTHER PUBLICATIONS

Waddell, T. G. and Ibach, D. M., "Modern Chemical Aphrodisiacs," *Indian J. Pharm. Sci.*, 51(3):79–82 (1989).
Buffam, J., "Pharmacosexology: The Effects of Drugs on Sexual Function, A Review," *J. of Psychoactive Drugs*, 14(1–2):5–44.
The Merck Index, Tenth Edition, pp. 692 and 696–697 (1983).
Carr, B. R. and Wilson, J. D. et al., "Disturbances of Menstruation and Sexual Function in Women" *Harrionson's Principles of Internal Medicine*, 12:299–301 (McGraw Hill Inc., New York) (1991).
McEvoy et al, AHFS, Drug Information pp. 1398–1399 (1987).
Nippon Nosan Kogyo, (From *Derwent Publications, Ltd.*, London, GB, Week 8226, 25 May 1982, Abstract No. AN 82–53897E & JP–57 083 254.).
Terapia Intr Medicamente et al., (From *Derwent Publications, Ltd.*, London, GB, Week 8834, 30 Apr. 1988, Abstract No. AN 88–240790 & RO–A–94 261.).

*Primary Examiner*—Allen J. Robinson
*Attorney, Agent, or Firm*—Hamilton, Brook, Smith & Reynolds

[57] ABSTRACT

A method of increasing vaginal lubrication comprising the use of hydriodic acid syrup. The hydriodic acid syrup is orally administered in the preferred embodiment.

4 Claims, No Drawings

METHOD OF INCREASING VAGINAL LUBRICATION

This application is a continuation-in-part of U.S. patent application Ser. No. 07/862,454, filed Apr. 2, 1992, now U.S. Pat. No. 5,231,423, issued Jan. 25, 1994 the teachings of which are incorporated herein by reference.

BACKGROUND OF THE INVENTION

The normal sexual response begins with sexual arousal which causes genital vasocongestion that results in vaginal lubrication. The lubrication is due to the formation of a transudate in the vagina which, in conjunction with genital congestion, produces the so-called orgasmic platform prior to orgasm. Sexual stimuli and healthy vaginal tissue are prerequisites for genital vasocongestion and vaginal lubrication. (HARRISON'S PRINCIPLES OF INTERNAL MEDICINE, 12th ed., ed. Wilson, J. D., et al. p. 301, McGraw-Hill Inc., New York (1991)).

Illnesses that impair neurological function, such as diabetes mellitus, may prevent normal sexual arousal. Pelvic diseases, such as vaginitis or endometriosis may also interfere with the normal sexual response. More commonly, decreased sexual response is due to psychological factors such as feelings of guilt, stresses such as anxiety, depression, fatigue or interpersonal conflicts which lead to failure of the vasocongestive response and prevent sufficient vaginal lubrication. (HARRISON'S PRINCIPLES OF INTERNAL MEDICINE, 12th ed., ed. Wilson, J. D., et al. p. 301, McGraw-Hill Inc., New York (1991)). In addition, vaginal lubrication in response to sexual stimuli may decrease as a woman ages. Insufficient, or absence of, vaginal lubrication may result in unsatisfying, or painful sexual relations.

Women experiencing stress may seek professional counseling by a therapist, physician or psychiatrist to overcome such problems and achieve normal sexual response. However, this option is often costly and time-consuming. Women suffering from a physical illness may be able to obtain relief through treatment of the underlying physical illness.

Alternatively, a number of creams or ointment preparations are commercially available for artificial lubrication. However, these preparations are often messy and inconvenient to use. Moreover, physical application of these artificial preparations are not always hygienic, and may introduce contaminants to the vaginal area, leading to irritation or infection. Thus, the need exists for a neat, hygienic, and convenient method of stimulating vaginal lubrication.

SUMMARY OF THE INVENTION

This invention relates to a method of increasing, or stimulating vaginal lubrication in an adult human female by using hydriodic acid in an aqueous solution. In the method of the present invention, the hydriodic acid is administered orally, as hydriodic syrup. Approximately 24 hours after oral administration, the amount of transudate present in the vagina is increased, resulting in increased lubrication of the vagina.

Oral administration of hydriodic acid to increase vaginal lubrication eliminates the problems associated with the application of creams and ointments to the vaginal area, thus simplifying preparation for sexual encounters and enhancing sexual satisfaction. Moreover, the risk of infection associated with external application of artificial lubricants is greatly reduced if not all together eliminated with the present invention.

DETAILED DESCRIPTION OF THE INVENTION

This invention is based upon the discovery that an aqueous solution of hydriodic acid can heighten sexual desire, including increasing the amount of transudate present in the vagina, resulting in increased vaginal lubrication.

Hydriodic acid is a clear colorless, or pale yellow liquid, an aqueous solution of hydrogen iodide, which is a gas at ordinary temperature. Hydriodic acid is also known as anhydrous hydriodic acid, hydrogen iodide (HI), hydrogen monoiodide or hydriodic. (The Merck Index, Merck & Co., Inc., 10th Ed. (1983)). Typically, hydriodic acid has been used as an expectorant, especially in the treatment of whooping cough (Pertussis).

As disclosed in the parent patent application, it has now been discovered that an aqueous solution of hydriodic acid has aphrodisiac properties, as confirmed through its use by an adult human female. The hydriodic acid of that, and the present, invention consists of hydriodic acid syrup comprised of hydriodic acid, water and dextrose. Hydriodic acid syrup was orally administered (ingested) to the subject. After approximately 24 hours, an aphrodisiac effect was experienced by the subject. The terms "aphrodisiac" or "heightened sexual desire", for the purposes of the present invention, refer to the following physical manifestations including clitoral swelling, nipple erection, contraction of the vaginal musculature, and a general tingling sensation.

Specifically, after oral administration of hydriodic acid syrup, the female subject experienced increased vaginal lubrication. The term "increased vaginal lubrication", as used herein, refers to an increased amount of transudate present in the vagina above the amount of transudate present in the unstimulated state.

Thus, the method of increasing vaginal lubrication in a human female described herein, comprises administering to a female in need of said treatment, an effective amount of hydriodic acid syrup, comprising hydriodic acid, water and dextrose. As described in the Exemplification below, an effective amount of hydriodic syrup for an adult human female weighing approximately 165 pounds, is about 0.5 to 3.0 teaspoons of hydriodic acid syrup in 8 ounces of tap water. It is understood that higher or lower amounts of hydriodic acid syrup would be used for heavier or lighter subjects as in the purview of one skilled in the art. Thus, as a result of Applicant's discovery, a method is now provided for a neat, hygienic and convenient means of increasing vaginal lubrication in a human female.

The invention will be further illustrated by the following non-limiting Exemplification:

Exemplification

Hydriodic acid solution was purchased from Eli Lilly and Company, of Indianapolis, Ind., referred to as hydriodic acid syrup. Hydriodic acid syrup can also be prepared by combining hydriodic acid with purified water and dextrose. For example, 140 ml of hydriodic acid is mixed with 550 ml of purified water. To this mixture, 450 g of dextrose is added and dissolved by agitation. Quantity sufficient of purified water is then added to bring the volume to 1000 ml, and the solution is filtered.

The syrup was administered orally to a female human, 52 years of age, weighing approximately 165 pounds. About 0.5 to 3.0 teaspoons of the hydriodic acid syrup was admixed with approximately 8 ounces of tap water and then ingested. An aphrodisiac effect, as defined above, including increased vaginal lubrication, was experienced within approximately 24 hours.

Equivalents

Those skilled in the art will recognize, or be able to ascertain, using no more than routine experimentation many equivalents to the specific embodiments of the invention described herein. Such equivalents are intended to be encompassed by the following claims.

The invention claimed is:

1. A method of increasing vaginal lubrication in an adult human female in need of said treatment, said treatment consisting essentially of increasing the amount of transudate present in the vagina, comprising orally administering to the female an effective amount of hydriodic acid syrup.

2. A method of claim 1 wherein the hydriodic acid syrup further comprises 140 ml of hydriodic acid, 550 ml of purified water and 450 g of dextrose.

3. A method of claim 1 wherein the effective amount of hydriodic acid syrup is approximately 0.5–3.0 teaspoons of hydriodic acid syrup.

4. A method of claim 3 wherein the effective amount of hydriodic acid syrup is added to approximately 8 ounces of water before administration.

* * * * *